(12) United States Patent
Bian et al.

(10) Patent No.: US 9,526,706 B1
(45) Date of Patent: Dec. 27, 2016

(54) METHOD OF USING DIHYDRO-RESVERATROL FOR TREATING ACUTE PANCREATITIS AND ASSOCIATED PULMONARY INJURY

(71) Applicant: Hong Kong Baptist University, Kowloon (HK)

(72) Inventors: Zhaoxiang Bian, Kowloon (HK); Siu Wai Tsang, Kowloon (HK); Hongjie Zhang, Kowloon (HK); Aiping Lu, Kowloon (HK); Albert Sun-Chi Chan, Kowloon (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 14/740,410

(22) Filed: Jun. 16, 2015

(51) Int. Cl.
*A61K 31/09* (2006.01)
*C07C 39/15* (2006.01)
*C07C 37/00* (2006.01)

(52) U.S. Cl.
CPC ............. *A61K 31/09* (2013.01); *C07C 37/003* (2013.01); *C07C 39/15* (2013.01)

(58) Field of Classification Search
USPC .......................................................... 514/721
See application file for complete search history.

(56) References Cited

PUBLICATIONS

Lu et al., Influence of Glucuronidation and Reduction Modifications of Resveratrol on its Biological Activities, 2013, ChemBioChem, 14, 1094-1104.*

* cited by examiner

*Primary Examiner* — Kristin Vajda
(74) *Attorney, Agent, or Firm* — Ware, Fressola, Maguire & Barber LLP (57) ABSTRACT

The present invention relates to a method of using trans-3,5,4'-trihydroxybibenzyl, also known as dihydro-resveratrol for treating acute pancreatitis in a subject in needs thereof. More particularly, the present invention relates to a method of using dihydro-resveratrol, its derivatives and/or chemical variants as a remedial agent. The present invention particularly relates to the amelioration of tissue injury for the management of acute pancreatitis associated pulmonary injury of a subject.

9 Claims, 10 Drawing Sheets

Figure 3A Control

Figure 3B Cerulein

Figure 3C Cerulein + D-Res 10mg

Figure 3D Cerulein + D-Res 20mg

Figure 3E Cerulein + D-Res 50mg

METHOD OF USING DIHYDRO-RESVERATROL FOR TREATING ACUTE PANCREATITIS AND ASSOCIATED PULMONARY INJURY

FIELD OF INVENTION

The present invention relates to a method of using dihydro-resveratrol for treating acute pancreatitis in a subject in needs thereof. More particularly, the present invention relates to a method of using a polyphenol derivative of the stilbenoid family, namely trans-3,5,4'-trihydroxybibenzyl, also known as dihydro-resveratrol as a remedial agent. The present invention particularly relates to the amelioration of tissue injury for the management of acute pancreatitis associated pulmonary injury of a subject.

BACKGROUND OF INVENTION

Acute pancreatitis is an inflammatory condition that happens as a sudden onset resulting from the premature activation of proteolytic zymogens occurring within the exocrine pancreas. The abnormally activated zymogens escape into the interstitium of the pancreas and cause autodigestion of the gland as reported in Grady T, Mah'Moud M, Otani T, Rhee S, Lerch M M, Gorelick F S. Zymogen proteolysis within the pancreatic acinar cell is associated with cellular injury. Am J Physiol. 1998; 275:G1010-7. The majority of cases of acute pancreatitis are caused by heavy alcohol consumption and gallstones. Genetics can be a factor in some cases as reported in Whitcomb D C, Gorry M C, Preston R A, Furey W, Sossenheimer M J, Ulrich C D, et al. Hereditary pancreatitis is caused by a mutation in the cationic trypsinogen gene. Nat Genet. 1996; 14:141-5; however, the cause can sometimes be idiopathic. Although acute pancreatitis is an inflammatory process originated in the pancreas, it often leads to multi-organ dysfunction syndrome that affects distant organs. The severe form of acute pancreatitis accompanies a high mortality rate of 15-20%, and hence continues to be an intricate problem in clinical management as reported in Charbonney, E., Nathens, A. B. 2008. Severe acute pancreatitis: a review. Surg Infect (Larchmt) 9, 573-578. The development of pulmonary injury or acute respiratory distress syndrome is the most frequent complication and potentially severe case amongst the systemic complications of acute pancreatitis. Acute lung injury is indeed the predominant cause of death in patients with severe acute pancreatitis as reported in McFadden, D. W. 1991. Organ failure and multiple organ system failure in pancreatitis. Pancreas 6 Suppl 1, S37-43. Unfortunately, there is no effective therapeutic procedure so that the mortality rate of severe acute pancreatitis stays relatively high.

It is an objective of the present invention to provide a method of using dihydro-resveratrol for treating acute pancreatitis in a subject.

Citation or identification of any reference in this section or any other section of this application shall not be construed as an admission that such reference is available as prior art for the present application.

SUMMARY OF INVENTION

Accordingly, the objective of the present invention relates to a method of using an effective amount of dihydro-resveratrol or its stilbenoid derivatives and/or chemical variants as a potential remedial agent for the treatment and/or alleviation of inflammatory conditions such as acute pancreatitis and associated systemic complications including pulmonary injury in a subject in needs thereof. Dihydro-resveratrol effectively reduces hyperamylasemia, acinar shrinkage, alveolar wall thickening and interstitial edema formation in the pancreas and lungs. Further, dihydro-resveratrol inhibits the production of pro-inflammatory cytokine tumor necrosis factor-alpha (TNF-α) and myeloperoxidase (MPO) activity while restoring pancreatic levels of glutathione. Importantly, oral administration of dihydro-resveratrol shows no adverse effects in the animal trial.

In a first embodiment of a first aspect of the present invention there is provided a method of treating acute inflammatory condition of the pancreas and associated systemic complications by administering to a subject in needs thereof a composition comprising an effective amount of a stilbenoid derivative which comprises a compound of formula (1), wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, and the derivatives or chemical variants thereof; or a mixture of said compound, the derivative and/or chemical variants thereof.

In a second embodiment of a first aspect of the present invention there is provided a method of treating acute inflammatory condition of the pancreas and associated systemic complications wherein the stilbenoid derivative is trans-3,5,4'-trihydroxybibenzyl, or dihydro-resveratrol, which is a compound of formula (2):

and the derivatives or chemical variants thereof; or a mixture of said compound, the derivative and/or chemical variants thereof.

In a third embodiment of the first aspect of the present invention there is provided a method of treating acute inflammatory condition of the pancreas and associated systemic complications wherein the subject is a human or an animal.

In a fourth embodiment of the first aspect of the present invention there is provided a method of treating acute inflammatory condition of the pancreas and associated systemic complications wherein the composition is administered orally.

In a fifth embodiment of the first aspect of the present invention there is provided a method of treating acute inflammatory condition of the pancreas and associated systemic complications wherein the acute inflammatory condition of the pancreas comprises all forms of acute pancreatitis and the associated systemic complications comprise pulmonary injury.

In a sixth embodiment of the first aspect of the present invention there is provided a method of treating acute inflammatory condition of the pancreas and associated systemic complications wherein said composition is administered at no less than 20 mg/kg to said subject for no less than 3 times a day.

In a seventh embodiment of the first aspect of the present invention there is provided a method of treating acute inflammatory condition of the pancreas and associated systemic complications wherein said composition is administered at no less than 3.24 mg/kg to said subject for no less than 3 times a day.

In a first embodiment of a second aspect of the present invention there is provided a method for preparing a compound of molecular formula $C_{14}H_{14}O_3$ and of formula (2), (2)

which is a stilbenoid derivative having a chemical name of trans-3,5,4'-trihydroxybibenzyl, through a hydrogenation of trans-resveratrol.

In a second embodiment of the second aspect of the present invention there is provided a method of preparing the compound of molecular formula $C_{14}H_{14}O_3$ and of formula (2) wherein the hydrogenation of trans-resveratrol comprises steps of
 stirring a solution of trans-resveratrol in anhydrous ethanol (EtOH) at room temperature under 5 atm $H_2$ pressure in the presence of 10% Pd/C for 8 hours;
 filtering off the catalyst from the stirred solution;
 evaporating the filtrate in vacuum to produce a residue;
 eluting the residue using silica gel chromatographic separation with petroleum ether and ethyl acetate (1:1) to produce dihydro-resveratrol.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the present invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

Among the several established animal models, repetitive intraperitoneal (i.p.) injection of cholecystokinin secretagogue, cerulein, is the most widely used and a highly reproducible method for the production of an experimental acute pancreatitis. Followed by a single shot of lipopolysaccharide (LPS), pulmonary injury characterized by neutrophil sequestration in the lung tissues and increased permeability of the alveolar membrane barrier is often observed as an acute pancreatitis associated complication. For the diagnosis of the onset of acute pancreatitis, bulky leakage of digestive enzymes, namely α-amylase, into the bloodstream is regarded as the principal pathological parameter. For evaluating the severity of acute pancreatitis and the associated pulmonary injury, morphological alterations of organ architecture including interstitial edema, cellular damage, leukocyte infiltration and hemorrhage are characterized as the histological and/or pathological parameters. Besides histological examination, aberrant MPO activity is often measured for assessing the severity of neutrophil-mediated inflammatory condition. Both the local and systemic inflammatory responses can be further confirmed by the high levels of pro-inflammatory cytokines present in the homogenates of affected tissues. Moreover, glutathione depletion, a defense mechanism, is one of the most common parameters for assessing the severity of tissue injury.

The subject to be treated by the method of this invention may be a human or an animal. The present invention is applicable to various forms of acute pancreatitis, and particularly to the acute pancreatitis associated systemic complications including pulmonary injury.

Dihydro-resveratrol, also known as trans-3,5,4'-trihydroxybibenzyl, is a derivative of polyphenol belonging to the family of stilbenoids, which are often obtained from plant extracts. In fact, dihydro-resveratrol is a phytoalexin produced by various plant species including *Orchidaceae* and *Cannabis sativa* L. against abiotic and biotic challenges, particularly in the case of fungal infection as reported in Fritzemeier, K. H., Kindl, H. 1983. 9,10-dihydrophenanthrenes as phytoalexins of *Orchidaceae*. Biosynthetic studies in vitro and in vivo proving the route from L-phenylalanine to dihydro-m-coumaric acid, dihydrostilbene and dihydrophenanthrenes. Eur J Biochem 133, 545-550.

The present invention relates to the usage of a polyphenol derivative of the stilbenoid family with formula 1:

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, to ameliorate tissue injury of the pancreas and lungs.

The present invention further relates to the usage of a stilbene compound containing trans-3,5,4'-trihydroxybibenzyl, also known as dihydro-resveratrol, see Compound 2:

to ameliorate tissue injury of the pancreas and lungs. In the present invention, this particular stilbenoid derivative was obtained as white powders through hydrogenation of trans-resveratrol.

Further, the invention is concerned with a process for the manufacture of the above compound, pharmaceutical preparations which contain such compound, and the use of this compound for the production of pharmaceutical preparations.

Figure 1:
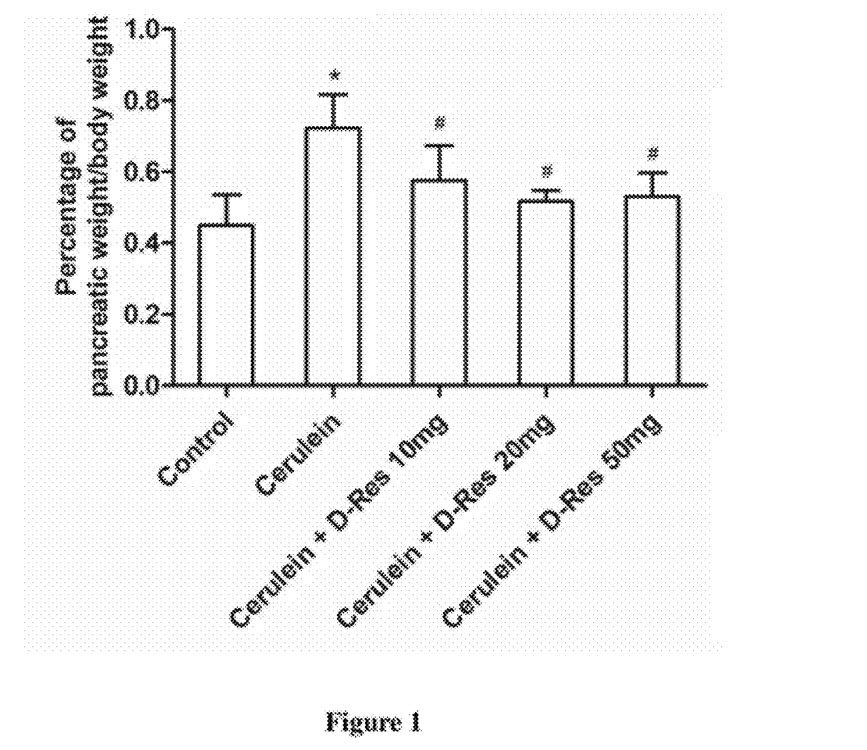
FIG. 1 shows the gain of water content in rats due to effect of pancreatic edema as a result of cerulein-induced acute pancreatitis. The obtained weights are expressed as a ratio percentage of pancreatic weight to body mass. A p-value of less than 0.05 is considered as statistically significant. *$p<0.05$ when comparing with control group whereas #$p<0.05$ comparing with cerulein group.
Figure 2A:
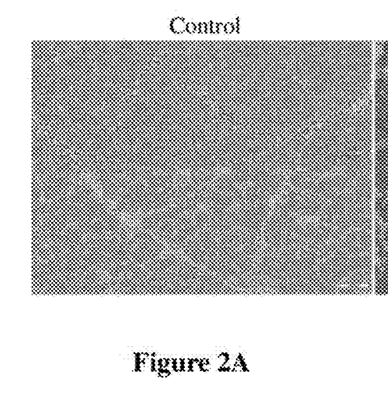
FIGS. 2A to 2F show the architecture and morphological alteration in pancreatic tissues of control group (FIG. 2A), cerulein group (FIG. 2B) and dihydro-resveratrol treatment groups (D-Res) (FIGS. 2C to 2F) by means of hematoxylin and eosin (H&E) staining. Images are shown with a scale bar of 50 μm.
Figure 2B:
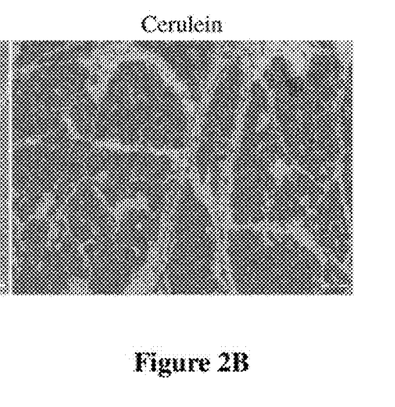
Figure 2C:
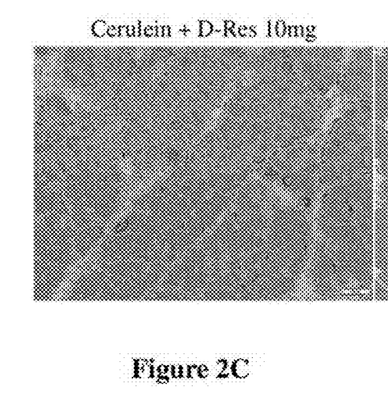
Figure 2D:
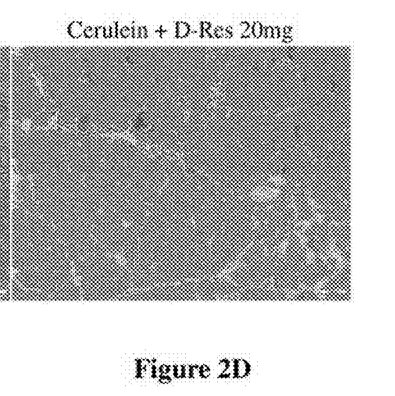
Figure 2E:
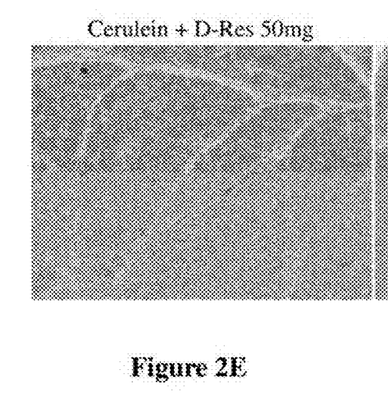
Figure 2F:
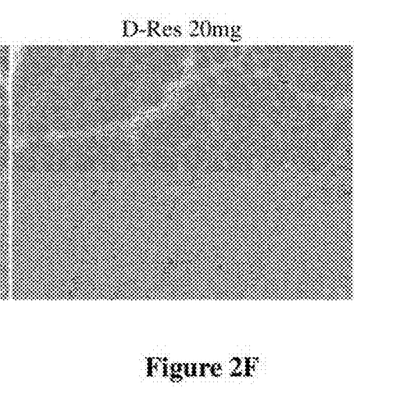
Figure 3A:
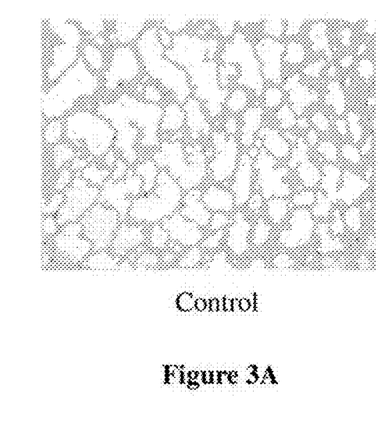
FIGS. 3A to 3E show the architecture and morphological alteration in pulmonary tissues of control group (FIG. 3A), cerulein group (FIG. 3B) and dihydro-resveratrol treatment groups (D-Res) (FIGS. 3C to 3E) by means of H&E staining Images are shown with a magnification of 200×.
Figure 3B:
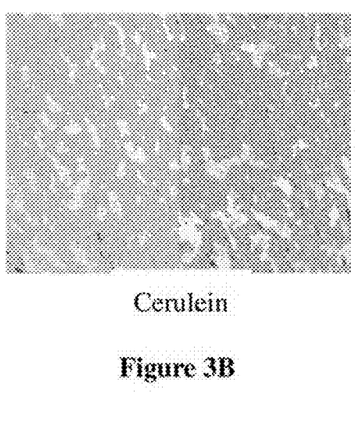
Figure 3C:
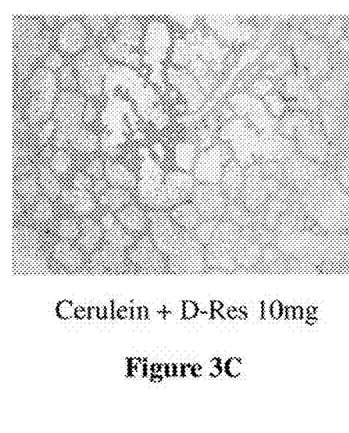
Figure 3D:
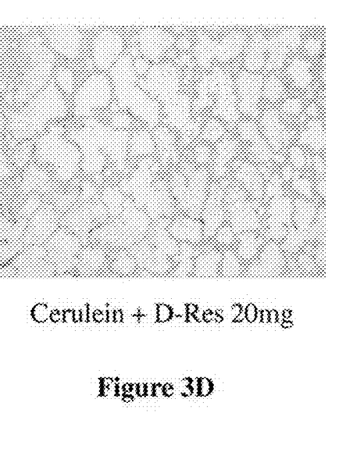
Figure 3E:
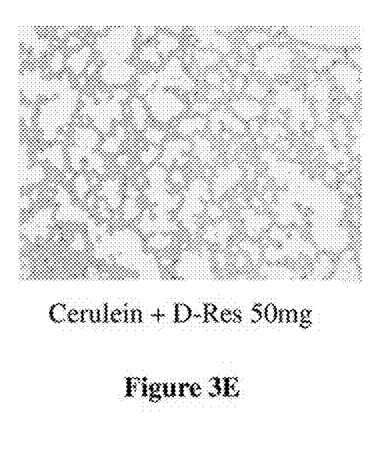

The oral administration of dihydro-resveratrol at an adequate dosage of not less than 20 mg/kg is shown to significantly ameliorate the severity of acute pancreatitis and associated pulmonary injury in cerulein-treated rats. In terms of pathological parameters, rats with acute pancreatitis are shown to have lessened pancreatic water content due to an attenuation of pancreatic edema (FIG. 1), lowered plasma level of α-amylase (Table 1), more intact acinar morphology (FIGS. 2C to 2F) and reduced thickening of alveolar wall and hemorrhage (FIGS. 3C to 3E).

TABLE 1

Plasma α-amylase activities are expressed as U/μl/minute.

|  | Control | Cerulein | Cerulein + D-Res 10 mg | Cerulein + D-Res 20 mg | Cerulein + D-Res 50 mg |
|---|---|---|---|---|---|
| mean | 0.1294 | 0.4846* | 0.2891 | 0.2498# | 0.2431# |
| S.D. | 0.03909 | 0.1457 | 0.05248 | 0.05593 | 0.06025 |

A p-value of less than 0.05 is considered as statistically significant and S.D. stands for standard derivation.
*p < 0.05 when comparing with control group whereas #p < 0.05 comparing with cerulein group.

Figure 4A:
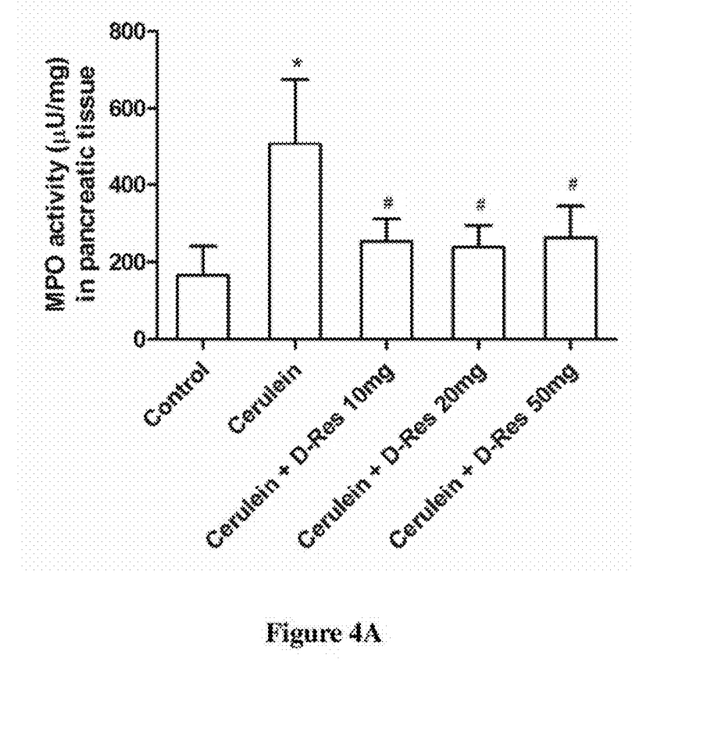
FIG. 4A shows the measurement of MPO activity which represents neutrophil sequestration in pancreatic tissues of control group, cerulein group and dihydro-resveratrol treatment groups (D-Res) by means of colorimetric spectrophotometry. A p-value of less than 0.05 is considered as statistically significant. *$p<0.05$ when comparing with control group whereas #$p<0.05$ comparing with cerulein group.
Figure 4B:
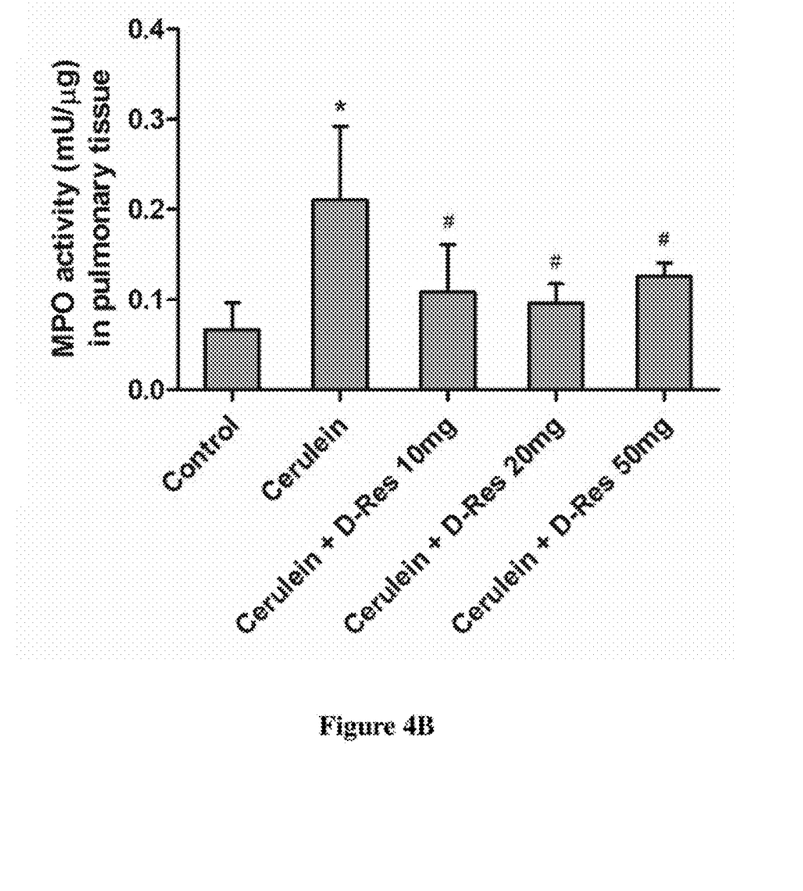
FIG. 4B shows the measurement of MPO activity which represents neutrophil sequestration in pulmonary tissues of control group, cerulein group and dihydro-resveratrol treatment groups (D-Res) by means of colorimetric spectrophotometry. A p-value of less than 0.05 is considered as statistically significant. *$p<0.05$ when comparing with control group whereas #$p<0.05$ comparing with cerulein group.
Figure 5A:
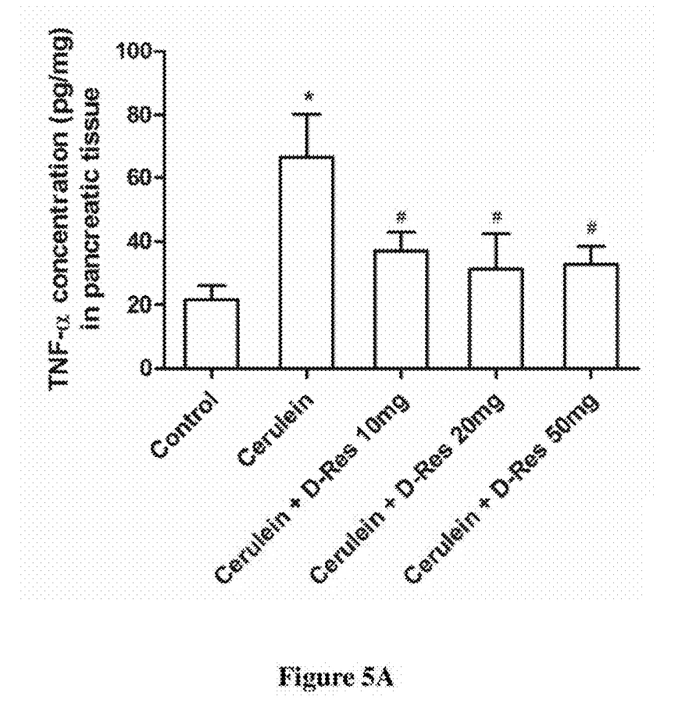
FIG. 5A shows the measurement of TNF-α level in pancreatic tissues of control group, cerulein group and dihydro-resveratrol treatment groups (D-Res) by means of enzyme-linked immunosorbent assay (ELISA). A p-value of less than 0.05 is considered as statistically significant. *p<0.05 when comparing with control group whereas #p<0.05 comparing with cerulein group.
Figure 5B:
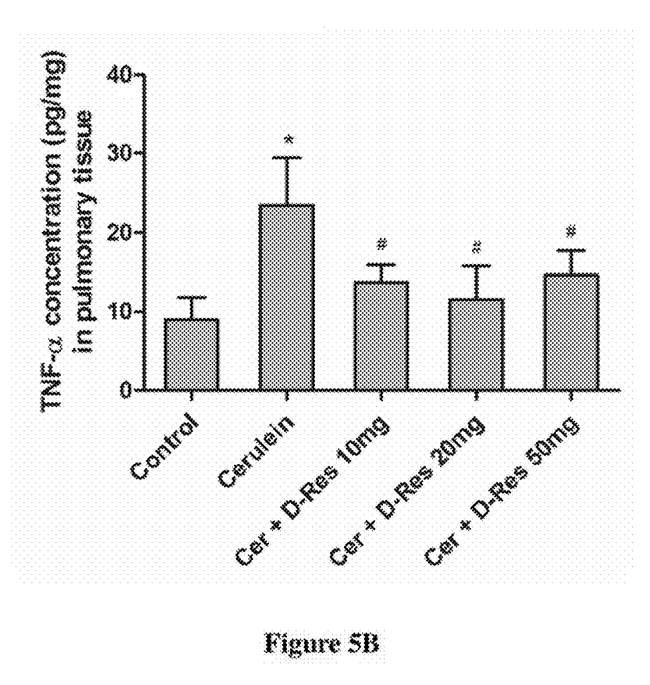
FIG. 5B shows the measurement of TNF-α level in pulmonary tissues of control group, cerulein group and dihydro-resveratrol treatment groups (D-Res) by means of ELISA. A p-value of less than 0.05 is considered as statistically significant. *p<0.05 when comparing with control group whereas #p<0.05 comparing with cerulein group.

Cerulein-induced elevated levels of neutrophil sequestration, which is quantified as the activity of MPO, are significantly suppressed in pancreatic and pulmonary tissues by the administration of dihydro-resveratrol (FIGS. 4A and 4B). Cerulein-induced elevated levels of TNF-α in the pancreas and lungs are significantly suppressed by the administration of dihydro-resveratrol (FIGS. 5A and 5B).

Figure 6A:
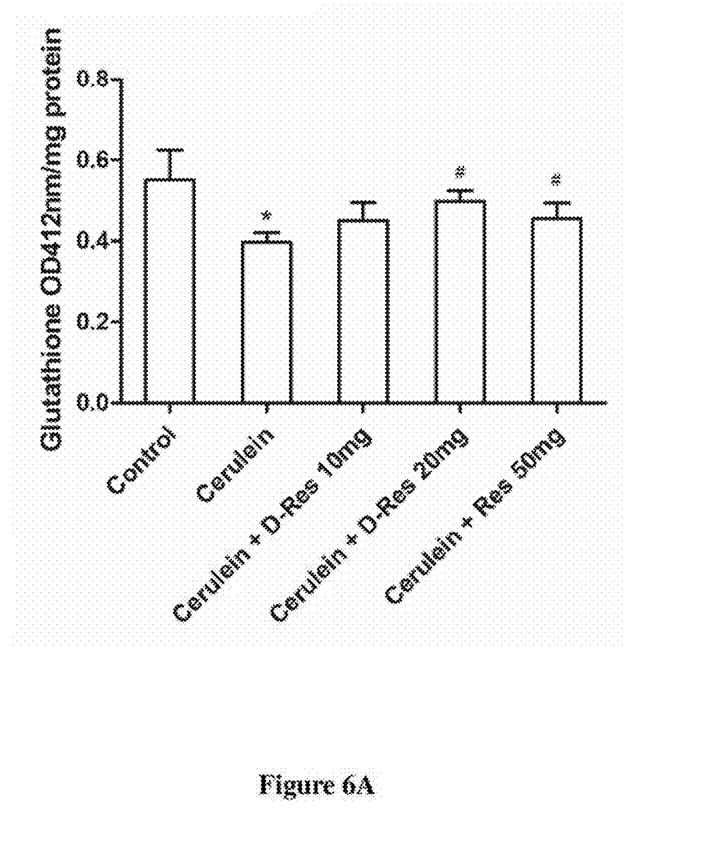
FIG. 6A shows the measurement of glutathione levels in pancreatic tissues of control group, cerulein group and dihydro-resveratrol treatment groups (D-Res) by means of colorimetric spectrophotometry. A p-value of less than 0.05 is considered as statistically significant. *p<0.05 when comparing with control group whereas #p<0.05 comparing with cerulein group.

Glutathione depletion is a distinctive sign of tissue injury. The cerulein-induced declined levels of glutathione in the pancreas are significantly restored by the administration of dihydro-resveratrol (FIG. 6A).

Figure 6B:
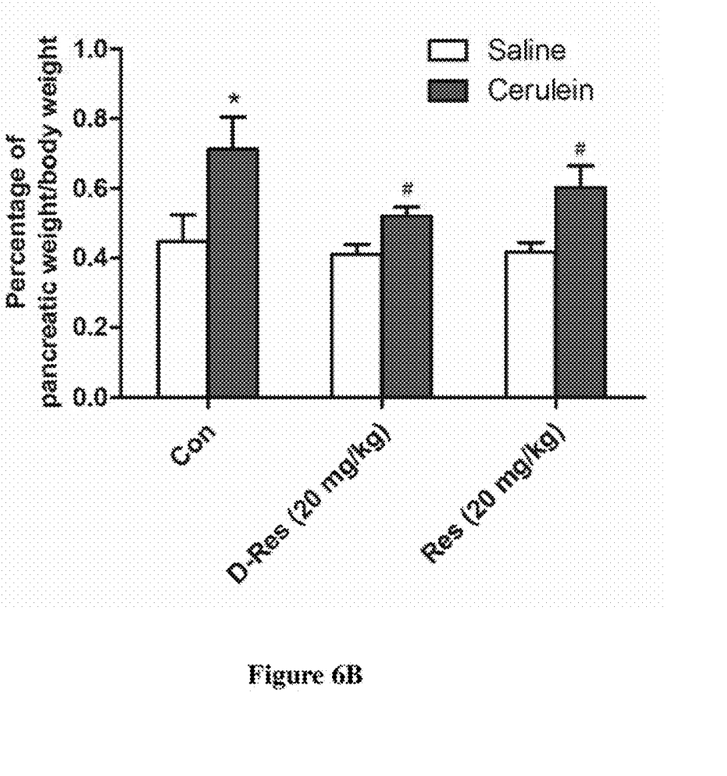
FIG. 6B shows the ameliorative effect of dihydro-resveratrol (D-res) and trans-resveratrol (Res) on reducing water content as a result of pancreatic edema in rats with cerulein-induced acute pancreatitis. The obtained weights are expressed as a ratio percentage of pancreatic weight to body mass. A p-value of less than 0.05 is considered as statistically significant. *p<0.05 when comparing with saline-treated control group (Con) whereas #p<0.05 comparing with cerulein-treated control group.

In the present invention, dihydro-resveratrol completely and easily dissolves in 0.5% (weight/volume, w/v) methanol whereas trans-resveratrol, with vigorous shaking, dissolves in 2.5% (w/v) methanol (Table 2). Thus, the solubility of dihydro-resveratrol is at least 5 times higher than that of trans-resveratrol. The ameliorative effect of dihydro-resveratrol was more promising than that of trans-resveratrol on reducing water content as a result of pancreatic edema in rats with cerulein-induced acute pancreatitis (FIG. 6B).

TABLE 2

Solubility of Dihydro-resveratrol and Trans-resveratrol in methanol.

|  | Trans-resveratrol | Dihydro-resveratrol |
|---|---|---|
| Methanol required (w/v) | 2.5% | 0.5% |

Figure 7:
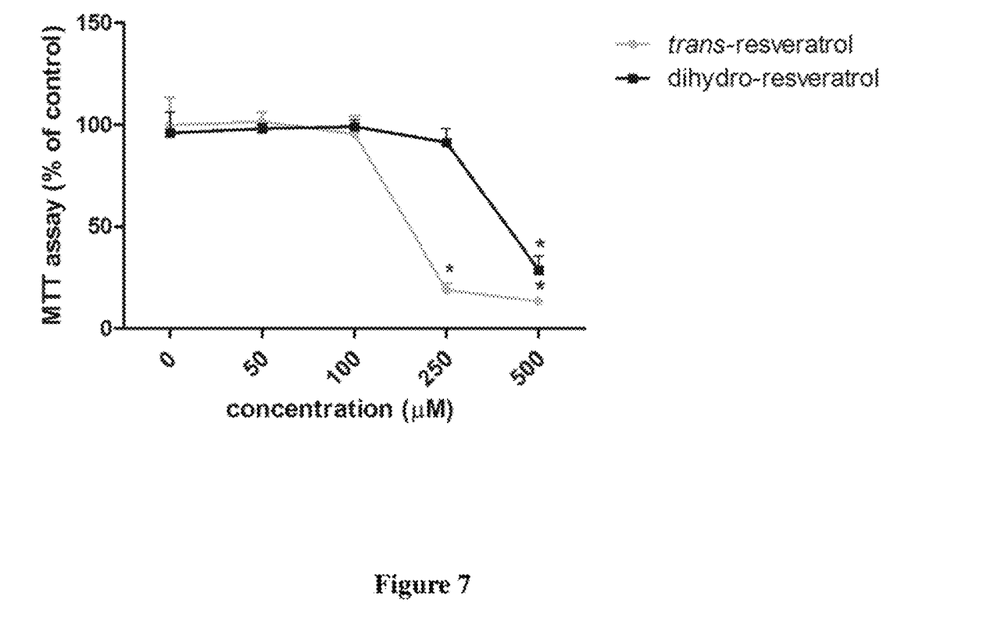
FIG. 7 shows the measurement of metabolic rates by means of MTT cell proliferation in pancreatic acinar cells treated with dihydro-resveratrol and trans-resveratrol. *p<0.05 when comparing with cells treated without dihydro-resveratrol or trans-resveratrol.

From the evaluation of mitochondrial metabolic rates by means of MTT assay, the cytotoxicity of dihydro-resveratrol in pancreatic acinar cells is determined to be approximately 500 μM whereas that of trans-resveratrol is roughly 250 μM (FIG. 7). Thus, the cytotoxicity of dihydro-resveratrol was 50% lower than that of trans-resveratrol.

Experiments

Preparation and structural identification of dihydro-resveratrol. The molecular formula of dihydro-resveratrol was established as $C_{14}H_{14}O_3$, which was obtained as white powders through hydrogenation of trans-resveratrol. A solution of trans-resveratrol (10 g, 43.8 mmol) in anhydrous EtOH (150 ml) was stirred at room temperature under 5 atm $H_2$ pressure in the presence of 10% Pd/C (0.2 g). The reaction was quenched after 8 hours (h), by filtering off the catalyst. The filtrate was evaporated in vacuum and the residue was subjected to silica gel chromatographic separation eluting with petroleum ether and ethyl acetate (1:1) to afford dihydro-resveratrol as white amorphous powder (9.6 g, 95% yield): HR-ESIMS ([M+1]+ m/z 231.1026, calcd 231.1016 for $C_{14}H_{15}O_3$); $^1$H NMR (methanol-d4, 400 MHz) δ 6.96 (2H, ABd, J=8.3 Hz), 6.67 (2H, ABd, J=8.4 Hz), 6.13 (2H, brd, J=2.2 Hz), 6.09 (1H, brt, J=2.2 Hz), 2.74 (2H, brdd, J=8.5, 5.6), 2.67 (2H, brdd, J=8.3, 5.2); $^{13}$C NMR (methanol-d4, 100 MHz) δ 159.2 (2C, s), 156.3 (1C, s), 145.6 (1C, s), 134.1 (1C, s), 130.3 (2C, d), 116.0 (2C, d), 108.1 (2C, d), 101.1 (1C, d), 39.6 (2C, t), 38.0 (2C, t).

Evaluation of biological activities. Sprague-Dawley rats aged 28 days weighing in the range of 70 to 90 g were randomly assigned into 6 groups of 6 to 8 individuals. The rats were housed with an ambient temperature of 23±2° C., a relative humidity of 60 to 80% and a 12-h light/dark cycle. Prior to the experiment, the rats were starved overnight but allowed with free access to water. Experimental acute pancreatitis was induced in the rats by six hourly i.p. injections of cerulein at the supramaximally stimulating dose (50 μg/kg) followed by a single dose of LPS at 7.5 mg/kg 1 h after the last cerulein injection, and this group of rats was designated as the cerulein group. The control group received injections of 0.9% saline instead of cerulein in the same volume and at same time intervals. The treatment groups given with cerulein and oral doses of dihydro-resveratrol (10, 20 or 50 mg/kg) were designated as Cerulein+D-res 10 or 20 or 50 mg/kg. The therapeutic intervention was given 30 minutes after the first cerulein injection for three consecutive hours. Upon scarification, pancreata were immediately removed, weighed, trimmed from fat and fixed in 4% paraformaldehyde-phosphate buffered saline overnight at 4° C. Samples were then processed, embedded in paraffin wax, sectioned and subjected to H&E staining. Levels of TNF-α in pancreatic and pulmonary samples were determined using commercial ELISA kits. Tissue homogenates were subjected to biochemical assays for the evaluation of MPO activity and glutathione content.

Functional intact acini were dissociated from pancreatic tissue using collagenase digestion with mild shearing forces. Acini were cultured in Dulbecco's modification of Eagle's medium (GIBCO) supplemented with 5% fetal bovine serum (GIBCO), 1% penicillin-streptomycin (GIBCO) in a 5% $CO_2$, 95% air humidified atmosphere at 37° C. LTC-14 cells were seeded at a density of $1×10^4$/well in a 96-well plate, and incubated with different concentrations of dihydro-resveratrol or trans-resveratrol (dissolved in DMSO) for 24 hours. MTT reagent was added to the cells at the end of the 24-hour treatment period. After a 3-hour reaction time, MTT products were dissolved in DMSO and absorbance at 570 nm was taken.

Results

After the induction of cerulein, the weight ratio of pancreas to body in the acute pancreatitis rats was drastically increased by roughly 60% when compared with the non-cerulein induced controls due to the occurrence of pancreatic edema. The oral administration of dihydro-resveratrol at an adequate dosage of not less than 20 mg/kg notably reduced the pancreatic edema as reflected by the significant decrease in the weight ratio of pancreas to body. The ameliorative effect of dihydro-resveratrol on reducing pancreatic edema was more promising than that of trans-resveratrol, the accredited antioxidant. Regarding the human dosage, the comparable dosage is 3.24 mg/kg based on the standard dosage conversion according to Reagan-Shaw S, Nihal M, Ahmad N (2008) Dose translation from animal to human studies revisited. FASEB J 22(3): 659-661.

When oral administration of dihydro-resveratrol was given, the focal expansion of the interlobular septae, cytoplasmic shrinkage and leukocyte infiltration in pancreatitic parenchyma was remarkably reduced whereas the pulmo- nary wall thickening and hemorrhage in lung tissues were significantly improved in the rats with cerulein-induced acute pancreatitis.

For a relief of inflammatory conditions of the pancreas and lungs, the levels of pro-inflammatory cytokine TNF-α as well as MPO activities were significantly reduced in the pancreatic and pulmonary tissues by the oral administration of dihydro-resveratrol.

The level of glutathione in cerulein-induced pancreatic tissue was depleted drastically by more than 50% when compared to the non-cerulein-treated control. The oral administration of dihydro-resveratrol significantly suppressed glutathione depletion in the cerulein-induced pancreata.

The solubility of dihydro-resveratrol in a methanol-based solvent was at least 5 times higher than that of trans-resveratrol. By assessing the mitochondrial metabolic rates of acini, the cytotoxicity of dihydro-resveratrol was shown to be approximately 500 µM whereas that of trans-resveratrol was roughly 250 µM. Thus, the cytotoxicity of dihydro-resveratrol was 50% lower than that of trans-resveratrol.

In a first embodiment of a first aspect of the present invention there is provided a method of treating acute inflammatory condition of the pancreas and associated systemic complications by administering to a subject in needs thereof a composition comprising an effective amount of a stilbenoid derivative which comprises a compound of formula (1), (1)

wherein $R_1$, $R_2$ and $R_3$ are each independently selected from an alkyl group. The term "alkyl", alone or in combination with other groups, includes reference to a straight chain alkyl moiety having 1, 2, 3, 4, 5 or 6 carbon atoms. The term is further exemplified by such groups as methyl, ethyl, propyl (n-propyl or isopropyl), butyl (n-butyl, sec-butyl and tert-butyl), pentyl, hexyl and the like, and the derivatives or chemical variants thereof; or a mixture of said compound, the derivative and/or chemical variants thereof.

In a second embodiment of a first aspect of the present invention there is provided a method of treating acute inflammatory condition of the pancreas and associated systemic complications wherein the stilbenoid derivative is trans-3,5,4'-trihydroxybibenzyl, or dihydro-resveratrol, which is a compound of formula (2):

(2)

and the derivatives or chemical variants thereof; or a mixture of said compound, the derivative and/or chemical variants thereof.

In a third embodiment of the first aspect of the present invention there is provided a method of treating acute inflammatory condition of the pancreas and associated systemic complications wherein the subject is a human or an animal.

In a fourth embodiment of the first aspect of the present invention there is provided a method of treating acute inflammatory condition of the pancreas and associated systemic complications wherein the composition is administered orally.

In a fifth embodiment of the first aspect of the present invention there is provided a method of treating acute inflammatory condition of the pancreas and associated systemic complications wherein the acute inflammatory condition of the pancreas comprises all forms of acute pancreatitis and associated systemic complications comprise pulmonary injury.

In a sixth embodiment of the first aspect of the present invention there is provided a method of treating acute inflammatory condition of the pancreas and associated systemic complications wherein said composition is administered at no less than 20 mg/kg to said subject for no less than 3 times a day.

In a seventh embodiment of the first aspect of the present invention there is provided a method of treating acute inflammatory condition of the pancreas and associated systemic complications wherein said composition is administered at no less than 3.24 mg/kg to said subject for no less than 3 times a day.

In a first embodiment of a second aspect of the present invention there is provided a method for preparing a compound of molecular formula $C_{14}H_{14}O_3$ and of formula (2), (2)

which is a stilbenoid derivative having a chemical name of trans-3,5,4'-trihydroxybibenzyl, through a hydrogenation of trans-resveratrol.

In a second embodiment of the second aspect of the present invention there is provided a method of preparing the compound of molecular formula $C_{14}H_{14}O_3$ and of formula (2) wherein the hydrogenation of trans-resveratrol comprises steps of
   stirring a solution of trans-resveratrol in anhydrous EtOH at room temperature under 5 atm $H_2$ pressure in the presence of 10% Pd/C for 8 hours;
   filtering off the catalyst from the stirred solution;
   evaporating the filtrate in vacuum to produce a residue;
   eluting the residue using silica gel chromatographic separation with petroleum ether and ethyl acetate (1:1) to produce dihydro-resveratrol.

INDUSTRIAL APPLICABILITY

The compounds of the present invention, stilbenoid derivative trans-3,5,4'-trihydroxybibenzyl, also known as dihydro-resveratrol, is a potent remedial agent useful for preparation of a medicament to effectively treat acute pancreatitis. The present invention particularly relates to amelioration of tissue injury for the management of acute pancreatitis and associated systemic complications including pulmonary injury.

What is claimed is:

1. A method of treating acute inflammatory condition of the pancreas and associated systemic complications by administering to a subject in need thereof a composition comprising an effective amount of a stilbenoid type compound of formula (1), (1)

or a derivative or variant of said stilbenoid type compound, wherein $R_1$, $R_2$ and $R_3$ in said stilbenoid type compound are each independently a hydrogen or an alkyl group, any said all group being a straight chain alkyl moiety having 1, 2, 3, 4, 5 or 6 carbon atoms.

2. The method of claim 1 wherein any said alkyl group is selected from the group consisting of methyl, ethyl, n-propyl, isopropyl, n-butyl, sec-butyl, tert-butyl, pentyl, and hexyl.

3. The method according to claim 1 wherein the stilbenoid derivative is trans-3,5,4'-trihydroxybibenzyl which is a compound of formula (2):

(2)

or its derivative or variants.

4. The method according to claim 1 wherein the subject is a human or an animal.

5. The method according to claim 1 wherein the composition is administered orally.

6. The method according to claim 1 wherein the acute inflammatory condition of the pancreas comprises all forms of acute pancreatitis and associated systemic complications comprising pulmonary injury.

7. The method according to claim 1 wherein said composition is administered at no less than 20 mg/kg to said subject for no less than 3 times a day.

8. The method according to claim 1 wherein said composition is administered at no less than 3.24 mg/kg to said subject for no less than 3 times a day.

9. A method for preparing a compound of molecular formula $C_{14}H_{14}O_3$ and of formula (2), (2)

which is a stilbenoid derivative having a chemical name of trans-3,5,4'-trihydroxybibenzyl, through a hydrogenation of trans-resveratrol, comprising the steps of:

stirring a solution of trans-resveratrol in anhydrous ethyl hydroxide at room temperature under 5 atm $H_2$ pressure in the presence of 10% Pd/C catalyst for 8 hours;

filtering off the catalyst from the stirred solution;

evaporating the filtrate in vacuum to produce a residue; and eluting the residue using a silica gel chromatographic separation with petroleum ether and ethyl acetate in a ratio of 1:1 to produce dihydro-resveratrol.

* * * * *